Figure 1:
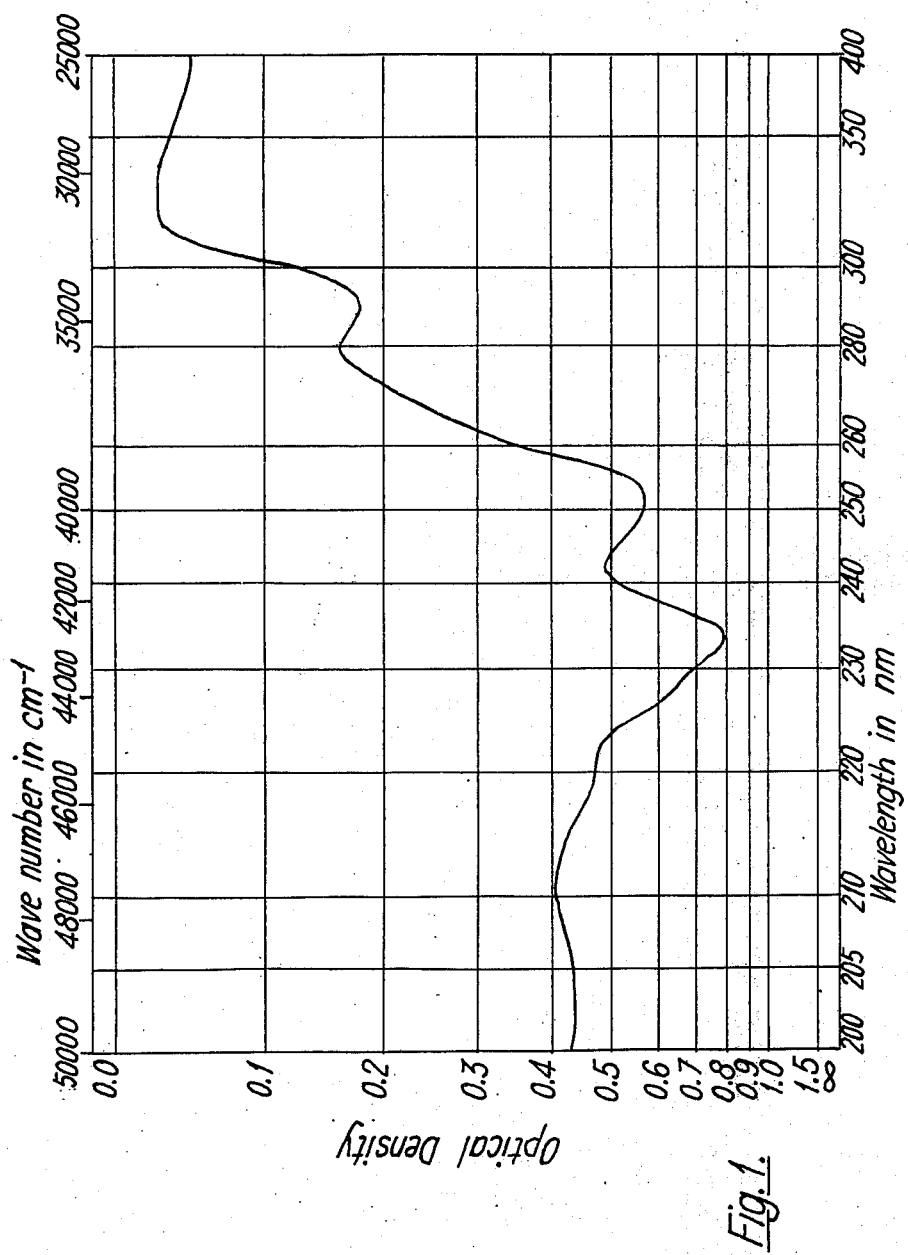

United States Patent [19]
Lunel et al.

[11] 3,987,028
[45] Oct. 19, 1976

[54] ANTIBIOTIC 20,798 R.P.
[75] Inventors: Jean Lunel; Jean Preud'Homme, both of Paris, France
[73] Assignee: Rhone-Poulenc S.A., Paris, France
[22] Filed: Mar. 4, 1969
[21] Appl. No.: 804,088

[30] Foreign Application Priority Data
Mar. 5, 1968  France ............................ 142443.68

[52] U.S. Cl. .............................. 536/17; 195/80 R; 260/365; 424/180; 424/181
[51] Int. Cl.² ........................................ C07H 15/00
[58] Field of Search ......... 260/210, 210 AB, 210 R, 260/365

[56]  References Cited
UNITED STATES PATENTS
2,736,725  2/1956  Ritter ........................ 260/210 AB
3,686,163  8/1972  Arcamone et al. ............ 260/210 AB Primary Examiner—Johnnie R. Brown
Attorney, Agent, or Firm—Stevens, Davis, Miller & Mosher

[57] ABSTRACT
The antibiotic 20,798 R.P. of the formula:

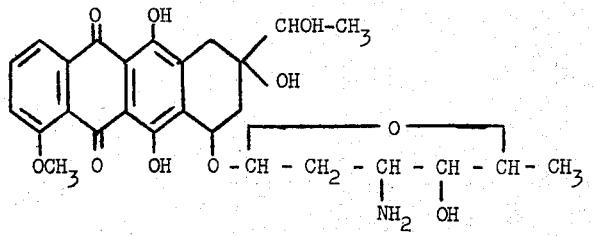

is of special interest because of its anti-tumor activity. The antibiotic is produced by culture of the microorganism *Streptomyces coeruleorubidus* (NRRL 3045).

4 Claims, 6 Drawing Figures

ANTIBIOTIC 20,798 R.P.

This invention relates to a new antibiotic hereinafter designated 20,798 R.P., to a process for its preparation and pharmaceutical compositions containing it.

The antibiotic 20,798 R.P. corresponds to the formula:

$$\text{I}$$

(Structure showing an anthracycline aglycone with OCH$_3$, O, OH, CHOH-CH$_3$, OH groups, linked via O to a sugar chain: O-CH-CH$_2$-CH(NH$_2$)-CH(OH)-CH-CH$_3$)

This antibiotic is produced alongside antibiotic 9865 R.P., of which the three principal constituents are designated by the numbers 13,057 R.P. (known by the name "daunorubicin"), 13,213 R.P. and 13,330 R.P., by culture of the microorganism *Streptomyces coeruleorubidus* (NRRL 3045) under the conditions described in British Pat. No. 985,598 entitled "Improvements in or relating to Antibiotics and their Preparation" granted to Rhone-Poulenc S.A. on an application filed May 16th 1963, claiming priority from French Pat. application No. 898,076 applied for on May 18th 1962, or corresponding Belgian Pat. No. 632,391, or in U.S. Pat. application Ser. No. 280,816 filed on May 16th 1963 by S. Pinnert, L. Ninet and J. Preud'Homme of common assignee. In the aforesaid British patent *Streptomyces coeruleorubidus* (NRRL 3045) is also given the synonym Streptomyces 31723 (NRRL 3045); a specimen of the microorganism has been deposited with the United States Department of Agriculture, Northern Regional Research Laboratory, at Peoria, Ill., U.S.A., under the number NRRL 3045. Specimens of the microorganism may be obtained freely from the U.S. Department of Agriculture, Agricultural Research Service, Fermentation Laboratory, Peoria, Ill., U.S.A.

The new antibiotic 20,798 R.P. is of a very special interest because of its pronounced anti-tumour activity. It forms acid addition salts. In the form of its hydrated hydrochloride, of overall formula $C_{27}H_{31}O_{10}N, HCl \cdot H_2O$, the antibiotic 20,798 R.P. has the following physico-chemical characteristics:

Appearance: orange-red needles
Melting point: 225°–230° C.
Solubility: it is soluble in water and alcohols, sparingly soluble in chloroform and practically insoluble in benzene and in diethyl ether.

Ultra-violet spectrum (determined with a solution of 10.09 mg./l. in ethanol containing 0.1% N hydrochloric acid):

shoulder at about 219 nm ($E_{1cm}^{1\%} = 465$), shoulder at about 228 nm ($E_{1cm}^{1\%} = 635$), absorption maximum at 234 nm ($E_{1cm}^{1\%} = 782$), absorption minimum at 242 nm ($E_{1cm}^{1\%} = 483$), absorption maximum at 252 nm ($E_{1cm}^{1\%} = 563$), shoulder at about 272 nm ($E_{1cm}^{1\%} = 200$), absorption minimum at 280 nm ($E_{1cm}^{1\%} = 158$), absorption maximum at 290 nm ($E_{1cm}^{1\%} = 178$) and absorption minimum at about 320 nm ($E_{1cm}^{1\%} = 28$), where nm is the abbreviation for nanometers.

This spectrum is shown in FIG. 1 of the accompanying drawings in which the abscissae give the wave length expressed in nanometers (lower scale) and the wave number in cm$^{-1}$ (upper scale), and the ordinate gives the optical density.

Visible spectrum (determined with a solution of 17.50 mg./l. in ethanol containing 0.1% N hydrochloric acid):

absorption maximum at 475 nm ($E_{1cm}^{1\%} = 143$), shoulder at about 533 nm ($E_{1cm}^{1\%} = 79$) and shoulder at about 553 nm ($E_{1cm}^{1\%} = 50$).

Figure 2:
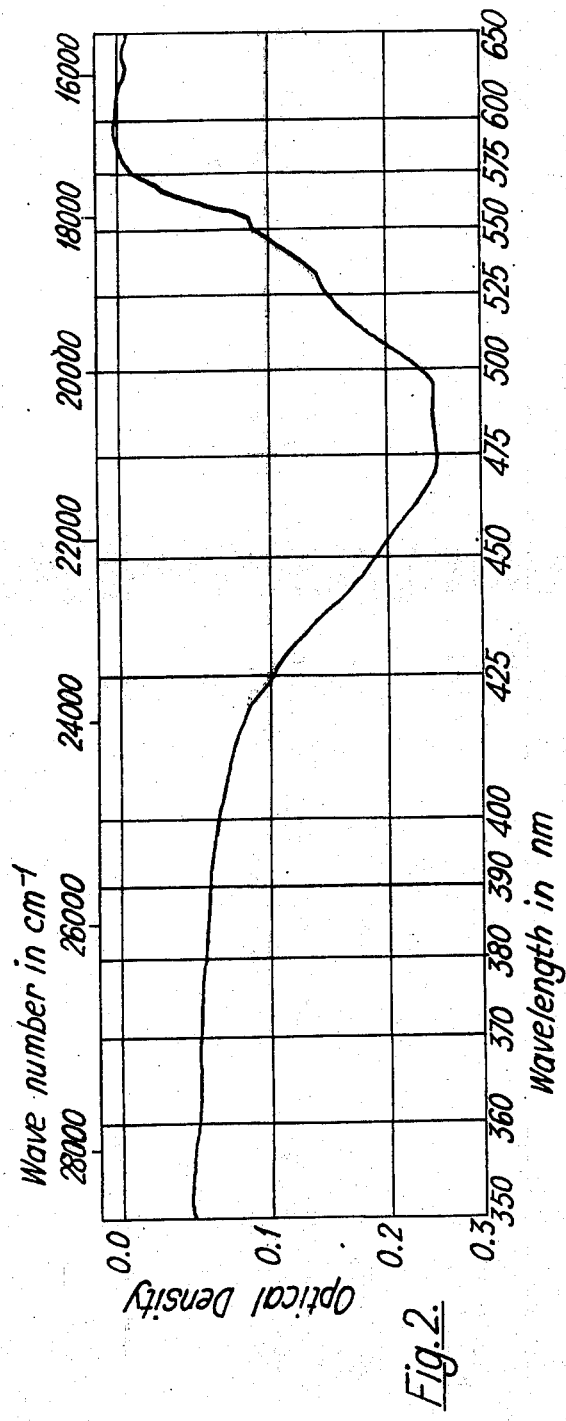

This spectrum is shown in FIG. 2 in which the abscissae give the wave length expressed in nanometers (lower scale) and the wave number in cm$^{-1}$ (upper scale), and the ordinate gives the optical density.

Figure 3:
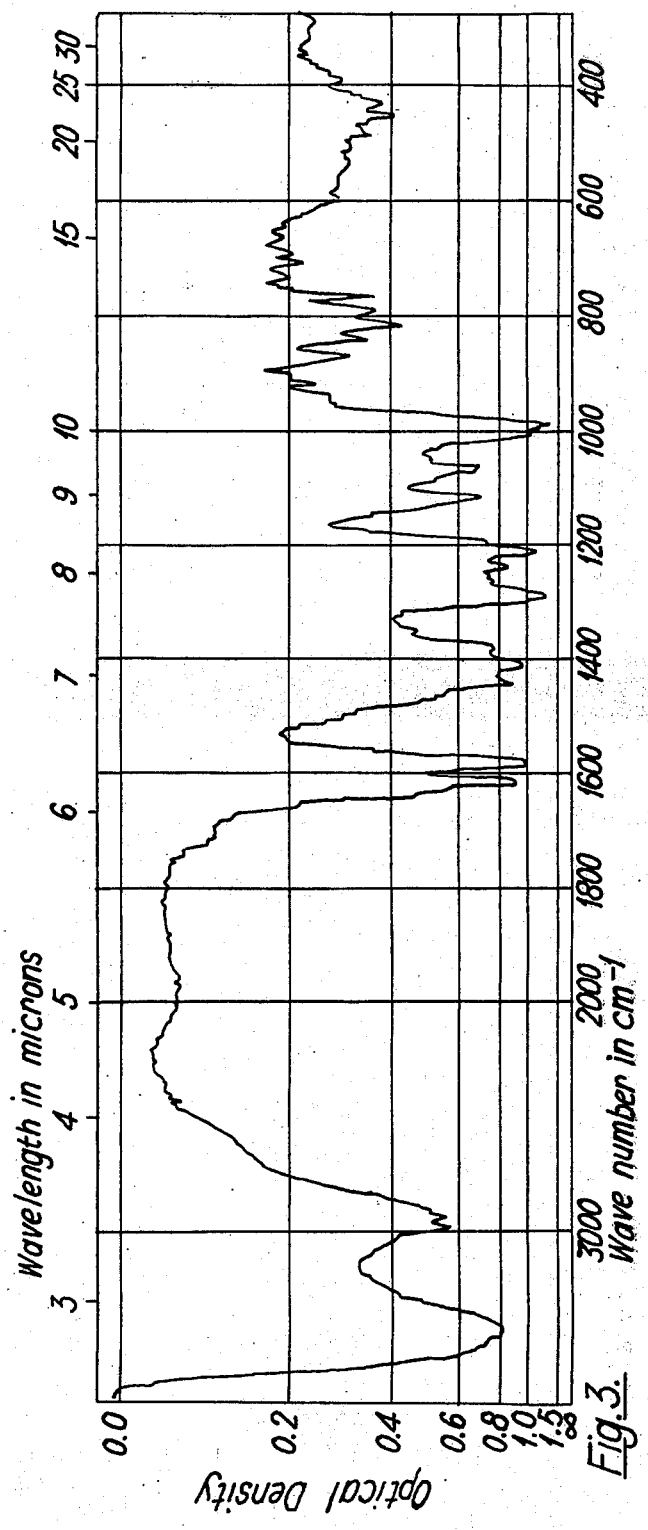

Infra-red spectrum (determined with tablets of a mixture with KBr):

This spectrum is shown in FIG. 3 in which the abscissae give the wavelength expressed in microns (upper scale) and the wave number in cm$^{-1}$ (lower scale), and the ordinate gives the optical density.

Table 1 below indicates the principal infra-red absorption bands of 20,798 R.P. hydrochloride.

TABLE I

| | | | |
|---|---|---|---|
| 3410 vs | 1540 sh | 1195 sh | 765 m |
| 3060 sh | 1510 sh | 1115 s | 750 sh |
| 2980 s | 1500 sh | 1080 sh | 730 w |
| 2940 s | 1490 sh | 1060 s | 710 m |
| 2850 sh | 1470 sh | 1045 w | 690 w |
| 2580 sh | 1460 sh | 1030 sh | 665 w |
| 2000 w | 1445 s | 1005 m | 600 m |
| 1960 w | 1430 w | 990 vs | 570 w |
| 1720 vw | 1410 vs | 950 vw | 535 w |
| 1710 w | 1380 s | 935 w | 505 w |
| 1655 sh | 1350 m | 915 m | 485 m |
| 1650 sh | 1285 vs | 905 w | 455 m |
| 1630 sh | 1260 vw | 870 m | 430 m |
| 1615 s | 1255 vw | 840 m | 390 m |
| 1580 vs | 1235 m | 820 m | 345 w |
| 1560 sh | 1210 vs | 790 m | 310 w | where
vs = very strong; s = strong; m = medium; w = weak; vw = very weak and sh = shoulder.

Optical rotation: $[\alpha]_D^{20} = +191 \pm 10°$ (c = 0.2, ethanol containing 0.1% N hydrochloric acid).

The antibiotic 20,798 R.P. can be identified by ascending chromatography on a thin layer of silica gel, using a mixture of benzyl alcohol-ethyl formate-formic acid-water (4-4-1-5 by volume) as the solvent. In this system 20,798 R.P. has an Rf of 0.57, daunorubicin has an Rf of 0.60 and the other constituents of antibiotic 9865 R.P. have an Rf above 0.60.

As with daunorubicin, 20,798 R.P. can be hydrolysed in an acid medium to yield an aglycone and an aminated sugar. The aglycone also forms part of the invention.

The study of the infra-red spectrum, nuclear magnetic resonance spectrum and mass spectrum enables the following formula II to be attributed to the aglycone of the antibiotic 20,798 R.P.:

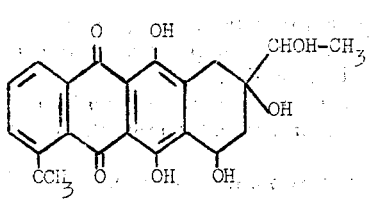

the formula of the aglycone of daunorubicin being:

[Structure III]

Physically, the aglycone of 20,798 R.P. is distinguished from the aglycone of daunorubicin by the differences in the Rf in chromatography on thin layers using various solvent systems and in particular:
system 1: chloroform-dioxan (95-5 by volume)
system 2: less dense phase of a mixture of ethyl acetate-diethylether-M/3 phosphate buffer of pH 4.8 (50-50-25 by volume)

| System | Aglycone of 20,798 R.P. Rf | Aglycone of daunorubicin Rf |
|---|---|---|
| 1 | 0.1 | 0.25 |
| 2 | 0.3 | 0.5 |

The aglycone of 20,798 R.P. shows the following physicochemical characteristics:
Appearance: orange-red needles
Melting Point: 285° C.
Solubility: it is sparingly soluble in ethyl acetate, chloroform and methanol, very sparingly soluble in benzene and practically insoluble in water, diethyl ether and hexane.
Ultra-violet spectrum (determined with a solution of 10.4 mg/1. in ethanol):
absorption maximum at 218 nm ($E_{1cm}^{1\%} = 500$), shoulder at about 228 nm ($E_{1cm}^{1\%} = 640$), absorption maximum at 233.5 nm ($E_{1cm}^{1\%} = 765$), absorption maximum at 251 nm ($E_{1cm}^{1\%} = 650$) and absorption maximum at 289 nm ($E_{1cm}^{1\%} = 183$).

Figure 4:
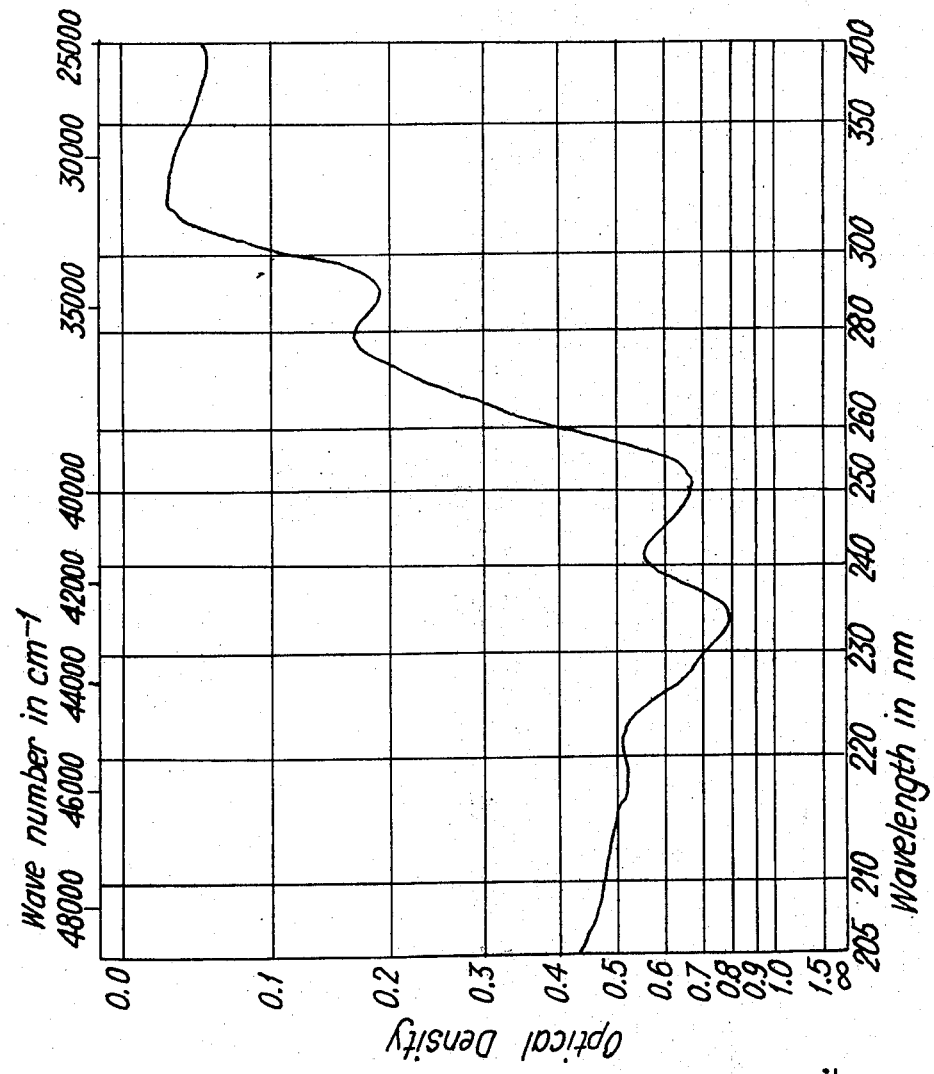

This spectrum is shown in FIG. 4 in which the abscissae give the wave length expressed in nanometers (lower scale) and the wave number in $cm^{-1}$ (upper scale), and the ordinate gives the optical density.

Visible spectrum (determined using a solution of 10.4 mg/1. in ethanol):
shoulder at about 470 nm ($E_{1cm}^{1\%} = 268$), absorption maximum at 495 nm ($E_{1cm}^{1\%} = 284$), absorption maximum at 528 nm ($E_{1cm}^{1\%} = 175$) and shoulder at about 570 nm ($E_{1cm}^{1\%} = 24$).

Figure 5:
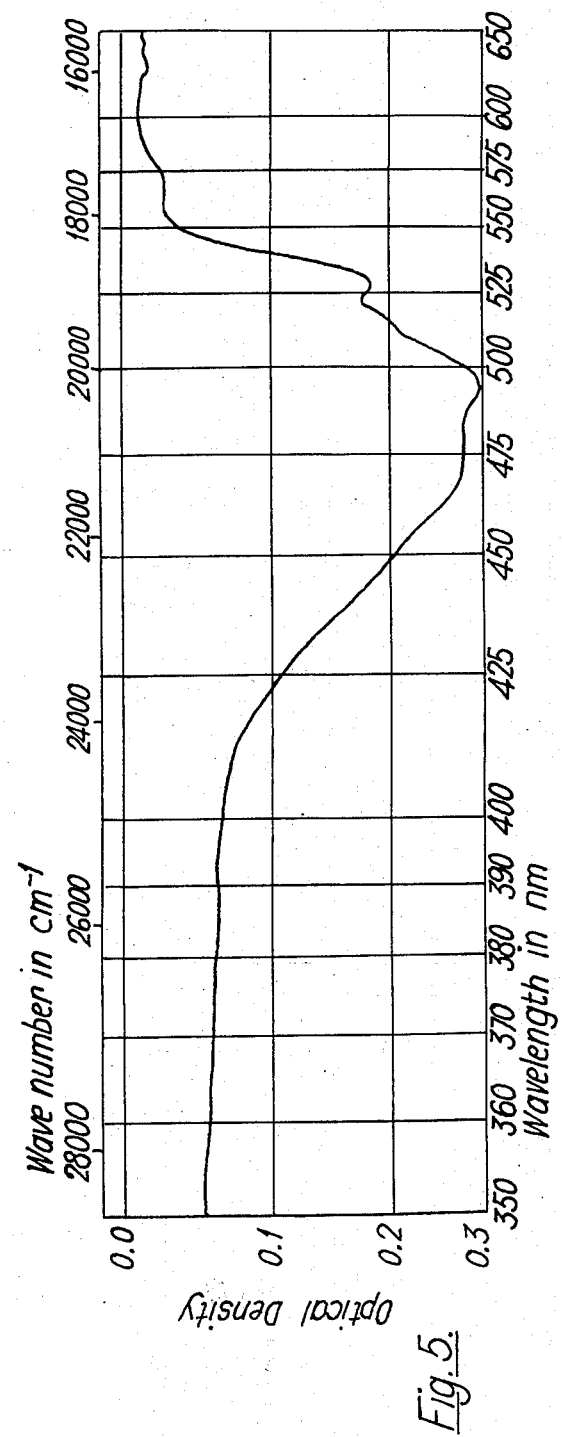

This spectrum is shown in FIG. 5 in which the abscissae give the wave length expressed in nanometers (lower scale) and the wave number in $cm^{-1}$ (upper scale), and the ordinate gives the optical density.

Figure 6:
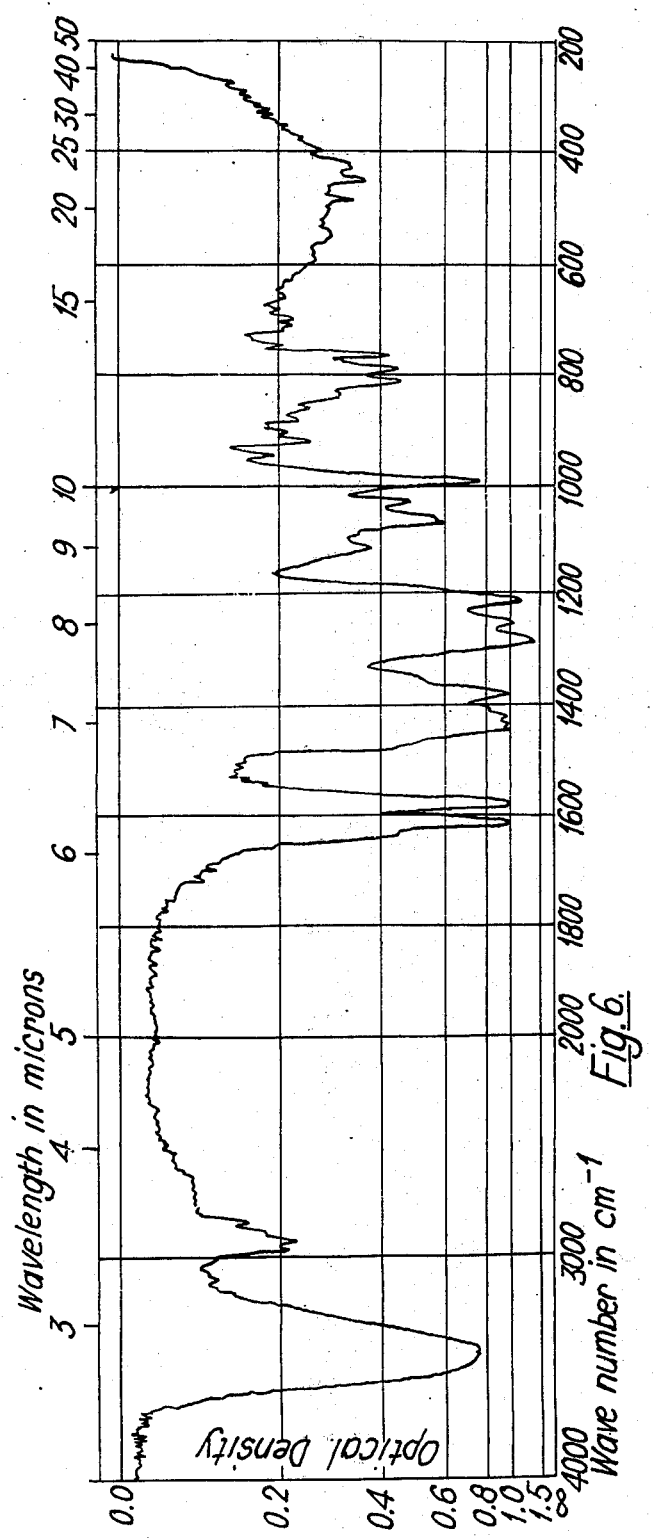

Infra-red spectrum (determined with tablets of a mixture with KBr):
This spectrum is shown in FIG. 6 in which the abscissae give the wavelength expressed in microns (upper scale) and the wave number in $cm^{-1}$ (lower scale), and the ordinate gives the optical density.

Table II below indicates the principal infra-red absorption bands of this product:

TABLE II

| | | | |
|---|---|---|---|
| 3540 sh | 1540 w | 1065 s | 745 w |
| 3500 sh | 1505 w | 1060 sh | 710 m |
| 3450 s | 1470 sh | 1030 m | 695 w |
| 3100 vw | 1445 s | 990 s | 680 vw |
| 2970 m | 1435 m | 940 s | 660 w |
| 2935 m | 1420 m | 915 m | 625 sh |
| 2890 w | 1380 s | 905 w | 615 sh |
| 2840 w | 1350 sh | 880 w | 590 w |
| 2650 sh | 1285 vs | 860 w | 545 w |
| 1655 sh | 1250 s | 840 vw | 500 vw |
| 1635 sh | 1210 s | 810 s | 485 w |
| 1615 vs | 1190 sh | 790 m | 450 m |
| 1585 vs | 1110 m | 765 m | 430 w | where vs = very strong; s = strong; m = medium; w = weak; vw = very weak and sh = shoulder.

The bacteriostatic activity of 20,798 R.P. was determined by one of the dilution methods usually employed for this purpose. For each microorganism the minimum concentration of antibiotic, which under specified conditions inhibits all visible development of the microorganism in an appropriate nutrient medium, was determined. The results of the various determinations are collected in Table III below, in which the minimum bacteriostatic concentrations are expressed in micrograms of substance per cc. of test medium.

TABLE III

| Bacterial strains tested | Minimal inhibitory concentration µg/cc. |
|---|---|
| Staphylococcus aureus, strain 209 P ATCC 6538 P | 100 |
| Streptococcus faecalis (Faculty of Pharmacy, Paris) | greater than 33 |
| Mycobacterium smegmatis ATCC 607 | 5.8 |
| Klebsiella pneumoniae ATCC 10,031 | greater than 330 |
| Klebsiella pneumoniae resistant to antibiotic 9865 R.P. | greater than 200 |
| Streptococcus pyogenes hemolyticus (strain Dig. 7, Institut Pasteur) | 11 |
| Diplococcus pneumoniae (strain Til, Institut Pasteur) | 6.1 |
| Sarcina lutea ATCC 9341 | 12 |
| Bacillus subtilis (ATCC 6633) | 21 |
| Mycobacterium phlei (Bacteriological Institute of Lyon) | 3.1 |
| Mycobacterium para-smegmatis (A 75, Lausanne) | 3.1 |
| Proteus X 19 | greater than 83 |
| Brucella bronchiseptica (CN 387 - Wellcome Institute) | 170 |
| Pasteurella multocida (A 125, Institut Pasteur) | 14 |
| Lactobacillus casei ATCC 7469 | 24 |
| Neisseria catarrhalis A 152 | greater than 28 |

TABLE III-continued

| Bacterial strains tested | Minimal inhibitory concentration μg/cc. |
|---|---|
| *Salmonella paratyphi A* (Lacasse, Institut Pasteur) | greater than 83 |

The anti-tumor activities of 20,798 R.P. have been demonstrated in the laboratory, where the antibiotic has shown itself to be particularly active against graftable tumours of mice such as the solid form of sarcoma 180 and of leucaemia L 1210.

The toxicity of 20,798 R.P. has been studied principally on mice. The 50% lethal dose or $LD_{50}$ was determined intra-peritoneally:

$LD_{50} = 6.5$ mg./kg. i.p. The 50% active dose or $AD_{50}$ was determined on mice by subcutaneous administration in the case of sarcoma 180: $AD_{50} = 0.75$ mg./kg. s.c., and by intraperitoneal administration in the case of leucaemia L 1210:

$AD_{50} = 0.8$ mg./kg. i.p.

According to a feature of the invention, a process for the production of antibiotic 20,798 R.P. comprises cultivating *Streptomyces coeruleorubidus* (NRRL 3045), or a 20,798 R.P.-producing mutant thereof, in a nutrient medium containing assimilable sources of carbon, nitrogen, and inorganic substances until substantial antibiotic activity is produced by the said microorganism in the said medium, and separating 20,798 R.P. formed during the culture from the medium. The culture of *Streptomyces coeruleorubidus* (NRRL 3045) may be carried out, as described in British Pat. Specification No. 985,598, by any method of aerobic or submerged culture, but the latter is preferred for reasons of convenience. For this purpose the various types of apparatus currently used in the fermentation industry are employed.

The following scheme for making a production culture is preferably used:

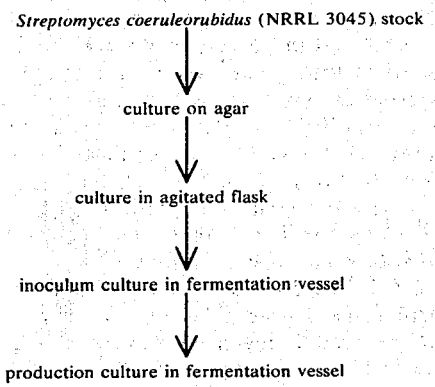

*Streptomyces coeruleorubidus* (NRRL 3045) stock
↓
culture on agar
↓
culture in agitated flask
↓
inoculum culture in fermentation vessel
↓
production culture in fermentation vessel The fermentation medium must contain assimilable sources of carbon, nitrogen, and inorganic substances and, optionally, growth factors, all these ingredients being introduced in the form of well-defined substances or as complex mixtures, such as those encountered in biological products of various origins.

Carbohydrates, such as glucose, lactose, sucrose, molasses, dextrins, starch, and other carbohydrates such as the sugar alcohols, e.g. mannitol, may be used as carbon sources, and also certain organic acids, e.g. lactic, citric, and tartaric acids. Certain animal or vegetable oils such as lard or soya oil may advantageously replace these various carbon sources, or be combined with them. A wide range of sources of assimilable nitrogen are suitable. They may be simple chemical substances such as nitrates, inorganic and organic ammonium salts, urea and amino acids. They may also be complex substances containing nitrogen principally in the form of protein, such as casein, lactalbumin, gluten and hydrolysates thereof, soya-, groundnut-, and fishmeals, meat extracts, yeast, distillers' solubles and corn-steep. Amongst the inorganic substances added, certain may exert a buffering or neutralising effect, such as alkali metal or alkaline earth metal phosphates and calcium and magnesium carbonates. Other inorganic substances contribute to the ionic equilibrium necessary for the development of *Streptomyces coeruleorubidus* (NRRL 3045) and the formation of the antibiotic, for example alkali metal and alkaline earth metal chlorides and sulphates. In addition, certain substances act as activators of the metabolic reactions of *Streptomyces coeruleorubidus* (NRRL 3045); these are the salts of zinc, cobalt, iron, copper and manganese.

The pH of the nutrient medium at the beginning of culture should be between 6.0 and 7.8, and preferably 6.5 to 7.5. The optimal temperature for the culture is 25°–28° C., but satisfactory production is obtained at temperatures between 23° and 35° C. The aeration of the fermentation medium may be varied over a fairly wide range of values but it has been found that aeration rates of 0.3 to 2 liters of air per minute per liter of medium are particularly suitable. The maximal yield of antibiotic is obtained after 2 to 5 days of culture, this period depending essentially on the medium used. From the foregoing it will be appreciated that the general conditions for the culture of *Streptomyces coeruleorubidus* (NRRL 3045) for the production of antibiotic 20,798 R.P. may be varied to a fairly wide degree.

20,798 R.P. can be isolated from the fermentation broths of *Streptomyces coeruleorubidus* (NRRL 3045) by various methods. The fermentation broth can be filtered at a pH of between 1.5 and 9. It is advantageous to carry out this operation using an acid medium, and particularly one acidified to a pH between 1.5 and 2 by means of oxalic acid. It is also possible to carry out the filtration at a pH between 2 and 7, preferably about 2, in the presence of an aliphatic alcohol containing 1 to 3 carbon atoms.

After the filtration procedures mentioned above, the mixture of antibiotics (constituents of 9865 R.P. and 20,798 R.P.) is obtained in aqueous or aqueous-alcoholic solution and it is then extracted with a water-immiscible organic solvent, such as butanol, methyl isobutyl ketone, ethyl acetate or chloroform, at a pH between 5.5 and 9, preferably about 8.5. This extraction may optionally be preceded by a treatment on an ion exchange resin, in which case the aqueous solution is adjusted to a pH of about 4 and then fixed onto a cationic carboxylic ion-exchange resin, preferably Amberlite IRC 50, in the acid form. Elution is then effected with an acid or saline aqueous-alcoholic solution, preferably with methanol containing 10% of water and 1% of sodium chloride. The eluate is concentrated to remove the alcohol and thereafter extracted as indicated above.

The fermentation broth may also be directly extracted with a water-immiscible organic solvent, such as butanol, ethyl acetate or chloroform, at a pH between 5.5 and 9, preferably about 8.5. In this case, all the antibiotic material passes into the organic phase which is separated from the aqueous phase by the usual processes.

When desired, the fermentation broth can, before the extraction procedures, be treated with an acid at a temperature between 10° and 75° C. for a period of from 48 hours to 30 minutes, the length of time varying inversely with the temperature, so as to enrich the antibiotic 9865 R.P. with daunorubicin. Under these conditions the antibiotic 20,798 R.P. is not hydrolysed. For acidification of the fermentation broth inorganic acids (hydrochloric, phosphoric or sulphuric acid) or organic acids (acetic or oxalic acid etc.) are suitable at various concentrations, but preferably hydrochloric acid or oxalic acid is used at concentrations of between 0.01N and 1N. The hydrolysis is preferably carried out for a period of from 15 hours to 1 hour at a temperature of from 20° C. to 50° C., the length of time varying inversely with the temperature.

Whatever the method of extraction chosen, the mixture of antibiotics (constituents of 9865 R.P. and 20,798 R.P.) is finally obtained in organic solution. It can be advantageous at this stage to carry out a purification by successively transferring the mixture of antibiotics into aqueous solution and then into organic solution by changing the pH. The mixture of crude antibiotics can then be isolated from the organic solution obtained in the last-mentioned operation by concentration or by precipitation with a poor solvent for the antibiotics such as hexane.

A particularly advantageous method of isolation consists in acidifying the organic solution to a pH of about 4, preferably by means of acetic acid, and then concentrating it to a small volume under reduced pressure. The addition of a poor solvent, such as hexane, to the resulting concentrate then causes the precipitation of the mixture of antibiotics.

The mixture of crude antibiotics can also be isolated by the formation of a salt, such as the hydrochloride, prepared by adding an acid, such as hydrochloric acid, to the organic solution of the antibiotics and precipitating the salt of the antibiotics by addition of a poor solvent for them such as acetone.

20,798 R.P. can be separated from the constituents of the antibiotic 9,865 R.P. by applying conventional methods such as chromatography on various adsorbents, counter-current distribution or partition between different solvents. The various counter-current distribution procedures can, of course, be preceded or followed by conventional purification procedures, notably by extraction or recrystallisation so as to yield 20,798 R.P. in a form which is suitable for the therapeutic application envisaged.

The following Examples illustrate the invention. In the following, the percentage of 20,798 R.P. is always determined by chromatography on a thin layer of silica gel using the solvent system benzyl alcohol-ethyl formate-formic acid-water (4-4-1-5 by volume) and direct fluorescimetric measurement of the chromatogram relative to a sample of the pure antibiotic.

EXAMPLE 1

A fermentation broth containing 20,798 R.P. is produced by the procedure described in Example 1 of British Pat. Specification No. 985,598 as follows:

A 170 liter fermentation vessel is charged with:

| | |
|---|---|
| corn steep | 2.400 kg. |
| sucrose | 3.600 kg. |
| calcium carbonate | 0.900 kg. |
| ammonium sulphate | 0.240 kg. |
| water to | 100 liters. |

This culture medium has a pH of 6.15. It is sterilised by passage of steam at 122° C. for 40 minutes. After cooling, the volume of the broth is 120 liters and the pH is 7.20. The medium is then seeded with 200 cc. of a culture in an agitated Erlenmeyer flask of *Streptomyces coeruleorubidus* (NRRL 3045). The culture is carried out for 27 hours at 26°–27° C. with agitation and aeration with sterile air. It is then suitable for seeding the production culture.

The production culture is carried out in an 800 liter fermentation vessel charged with the following:

| | |
|---|---|
| soya flour | 20 kg. |
| distillers' solubles | 2.500 kg. |
| starch | 10 kg. |
| soya oil | 2.500 liters |
| sodium chloride | 5 kg. |
| water to | 465 liters. |

The pH of the medium thus obtained is adjusted to 7.20 with concentrated sodium hydroxide solution (400 cc.). The medium is then sterilised by the passage of steam at 122° C. for 40 minutes. After cooling, the volume of the broth is 500 liters and the pH is 6.75. It is then seeded with 50 liters of the culture from the 170 liter fermentation vessel. Culture is carried out at 28° C. for 67 hours with agitation and aeration with sterile air. The pH of the medium is then 7.40 and the volume of the ferementation broth is 520 liters.

Oxalic acid (30 g. per liter) is added to the fermentation broth (400 liters) and it is then heated at 50° C. for 1 hour with stirring throughout. A filtration aid (12 kg.) is added and the mixture at 50° C. is filtered on a filter press and the filter cake washed with water at 50° C. The filtrate, having a volume of 475 liters, is cooled to +5° C. The pH is adjusted to 4.5 by addition of concentrated sodium hydroxide solution. The filtrate is thereafter passed through a column containing Amberlite I RC 50 (15 liters) in the acid form. The filtrate passes through the Amberlite bed in an upward direction at a flow rate of 45 liters/hour. The column is thereafter washed with water (150 liters) at the rate of 45 liters/hour, circulating in an upward direction. The column is then washed with a solution (225 liters) of methanol containing 10% water, circulating in a downward direction, at a flow rate of 45 liters/hour. The washings are discarded and the column is eluted with a solution of the following composition:

| | |
|---|---|
| sodium chloride | 10 g., |
| water | 100 cc., |

-continued

| methanol to make up to | 1000 cc. |

The eluate, which contains the greater part of the antibiotics, has a volume of 120 liters. It is concentrated under reduced pressure at 35° C. to a volume of 10 liters. The concentrate is successively extracted at pH 8.5 with chloroform (2 × 12 liters). The chloroform solution is concentrated under reduced pressure to a volume of 200 cc.; n-butanol (0.8 liters) is added and the resulting solution again concentrated under reduced pressure to a volume of 0.4 liters. 2N Hydrochloric acid (20 cc.) is added to this solution with stirring throughout. The acidified solution is heated to 65° C. and acetone (600 cc.) at 50° C. is added slowly. A mixture of crystalline hydrochlorides of the antibiotics (15 g.) is obtained.

This mixture contains 20% of 20,798 R.P. and 70% of daunorubicin.

EXAMPLE 2

The mixture of the hydrochlorides of the antibiotics obtained in Example 1 (15 g.) is dissolved, with stirring, in a mixture of chloroform-water (1-1 by volume; 600 cc.). The pH is adjusted to 8.5 by addition of N sodium hydroxide solution (18 cc.). This system is subjected to a counter-current distribution of 4 transfers in 1 liter ampoules. The heavy phase (solvent) is used as the mobile phase and the light phase (aqueous phase) as a stationary phase, and in each case 300 cc. of each phase are employed. The aqueous phase from ampoule 1 (solution A), the solvent phase from ampoule 5 (solution B) and the mixture of aqueous phase - solvent phase from ampoules 2, 3 and 4 are treated separately.

Solution A is successively extracted with a mixture of chloroform-n-butanol (1-1 by volume; 2 × 150 cc.) at pH 8.5. The extracts are concentrated under reduced pressure to a volume of 30 cc. The butanol solution thus obtained is adjusted to pH 3 by slowly adding n-butanol saturated with N hydrochloric acid (15 cc.). The hydrochloride of 20,798 R.P. crystallises. The crystals are filtered off, washed and dried to yield the hydrochloride of 20,798 R.P. (1 g.).

Solution B is concentrated to a volume of 30 cc. and thereafter treated like solution A. The hydrochloride of daunorubicin (3.9 g.) is obtained.

The mixture of ampoules 2,3 and 4 is concentrated to a volume of 200 cc. n-Butanol (600 cc.) is added and the solution concentrated to a volume of 100 cc. On addition of hexane (1000 cc.), a mixture (8 g.) containing 20% of 20,798 R.P. and 70% of daunorubicin is obtained.

EXAMPLE 3

The hydrochloride of 20,798 R.P. (2.6 g.) obtained as described in Example 2 is dissolved in a mixture of dioxan-water (4-1 by volume; 31.6 cc.). Anhydrous dioxan (200 cc.) is added slowly, whilst stirring slowly, in order to cause the hydrochloride of 20,798 R.P. to crystallise. The crystals are filtered off and washed with anhydrous dioxan (10 cc.) The crystals are dried for 15 hours at 50° C. under reduced pressure. The pure hydrochloride of 20,798 R.B. (2.06 g.) is obtained in a yield of 79%. This product has the following elementary composition:

C = 54.8%, H = 6.0%, O = 31.9%, N = 2.5%, Cl = 5.8%, $H_2O$ = 3.0%.

EXAMPLE 4

The product obtained in Example 3 (100 mg.) is dissolved in a mixture of methanol-N sulphuric acid (1-1 by volume). The solution is heated for 1 hour on a boiling water-bath. On cooling, crystals are obtained which are filtered off, washed and dried. The aglycone of 20,798 R.P. (36 mg.), melting at 285° C., is obtained. The present invention includes within its scope pharmaceutical compositions comprising 20,798 R.P. in association with a compatible pharmacologically acceptable carrier and/or a compound which may itself by physiologically active, for example an antibiotic. These compositions may be made up in any pharmaceutical form appropriate for the route of administration in question.

Solid compositions for oral administration include compressed tablets, pills, dispersible powders, and granules. In such solid compositions, the new antibiotic is admixed with at least one inert diluent such as calcium carbonate, potato starch, alginic acid, or lactose. The compositions may also comprise, as is normal practice additional substances other than inert diluents, e.g. lubricating agents, such as magnesium stearate. Liquid compositions for oral administration include pharmaceutically acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing the antibiotic with or without the addition of diluents or excipients.

Preparations according to the invention for parenteral administration include sterile aqueous or non-aqueous solutons, suspensions, or emulsions. Examples of non-aqueous solvents or suspending media are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilised by, for example, filtration through a bacteria-retaining filter, by incorporation in the compositions of sterilising agents, by irradiation, or by heating. They may also be manufactured in the form of sterile solid compositions, which can be dissolved in sterile water or some other sterile injectable medium immediately before use.

The percentage of active ingredient in the compositons of the invention may be varied, it being necessary that it should constitute a proportion such that a suitable dosage for the therapeutic effect desired shall be obtained. Obviously several unit dosage forms may be administered at about the same time. The results obtained with 20,798 in standard animal tests for anti-tumour activity and the close relationship of its molecular structure to the clinically used daunorubicin, imply that it will be useful in human therapy, particularly against acute lymphoblastic and myeloblastic leucaemias, when administered intravenously at daily doses of between 0.1 and 2 mg. for an adult; a composition for injection for example, consists of a solution of 0.1 mg/cc. of active substance in physiological serum. For oral treatment, the doses are generally between 1 and 10 mg. of the antibiotic per day for an adult. The compositons for oral administration are preferably tablets.

The following Example illustrates pharmaceutical compositions according to the invention.

EXAMPLE 5

Tablets containing 1 mg. of active product and having the following composition are prepared by a conventional method:

| | |
|---|---|
| 20,798 R.P. (hydrochloride) | 0.001 g. |
| starch | 0.081 g. |
| precipitated silica | 0.016 g. |
| magnesium stearate | 0.002 g. |

We claim:
1. An antibiotic substance having the formula:

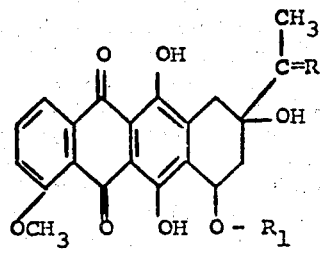

wherein R is

and $R_1$ is selected from the group consisting of the daunosaminil radical

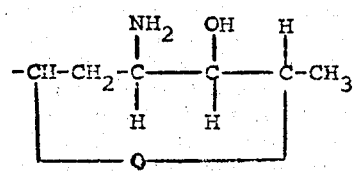

and of hydrogen, and its salts with pharmaceutically acceptable non-toxic acids.

2. The compound of claim 1, which is dihydrodaunomycin.
3. The compound of claim 1, which is dihydrodaunomycin hydrochloride.
4. The compound of claim 1, which is dihydrodaunomycinone.

* * * * *